(12) United States Patent
Jones et al.

(10) Patent No.: US 12,262,934 B2
(45) Date of Patent: Apr. 1, 2025

(54) BIPOLAR ELECTROSURGICAL INSTRUMENTS

(71) Applicant: GYRUS MEDICAL LIMITED, Cardiff (GB)

(72) Inventors: Lewis Jones, Cardiff (GB); Wayne Williams, Penarth (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 389 days.

(21) Appl. No.: 16/411,565

(22) Filed: May 14, 2019

(65) Prior Publication Data

US 2019/0380765 A1 Dec. 19, 2019

(30) Foreign Application Priority Data

Jun. 13, 2018 (GB) .................................. 1809683

(51) Int. Cl.
*A61B 18/12* (2006.01)
*A61B 18/00* (2006.01)
*A61B 18/14* (2006.01)

(52) U.S. Cl.
CPC ...... *A61B 18/1206* (2013.01); *A61B 18/1442* (2013.01); *A61B 2018/00404* (2013.01);
(Continued)

(58) Field of Classification Search
CPC ............ A61B 18/1206; A61B 18/1442; A61B 18/1445; A61B 2018/0063; A61B 2018/00875; A61B 2018/126; A61B 2017/00026; A61B 2090/064; A61B 2090/061; A61B 17/320092; A61B 2018/1233; A61B 2018/00589; A61B 2018/00767; A61B 2018/00684; A61B 2018/00702; A61B 2018/00678; A61B 2018/00755; A61B 2018/00791; A61B 2018/1455; A61B 2018/00994; A61B 2018/00666; A61B 2017/00017;
(Continued)

(56) References Cited

U.S. PATENT DOCUMENTS

2007/0173804 A1* 7/2007 Wham ............... A61B 18/1206
606/34
2007/0173813 A1* 7/2007 Odom ................ A61B 18/1445
606/51
(Continued)

OTHER PUBLICATIONS

Nov. 26, 2018 Search Report issued in European Patent Application No. GB1809683.4.

*Primary Examiner* — Khadijeh A Vahdat
*Assistant Examiner* — Marina Delaney Templeton
(74) *Attorney, Agent, or Firm* — Oliff PLC

(57) ABSTRACT

A bipolar surgical instrument (1) comprises a body (2), first and second opposed jaws (18, 20) located at the distal end of a shaft (10), the first jaw (18) being movable with respect to the second jaw (20) between an open position in which the first and second jaws (18, 20) are spaced apart from one another, and a closed position in which the first and second jaws (18, 20) are adjacent one another. The first and second elongate jaw members (18, 20) have respective first and second electrodes. A controller is operable to determine a mode of operation depending upon a measurement of impedance between the first and second jaws.

8 Claims, 6 Drawing Sheets

(52) U.S. Cl.
  CPC .............. *A61B 2018/0063* (2013.01); *A61B 2018/00666* (2013.01); *A61B 2018/00702* (2013.01); *A61B 2018/00827* (2013.01); *A61B 2018/00875* (2013.01); *A61B 2018/00892* (2013.01); *A61B 2018/126* (2013.01); *A61B 18/1445* (2013.01)

(58) Field of Classification Search
  CPC ......... A61B 2017/320095; A61B 2017/00084; A61B 2017/320094; A61B 2017/00022; A61B 2017/2927
  See application file for complete search history.

(56) References Cited

U.S. PATENT DOCUMENTS

| | | | | |
|---|---|---|---|---|
| 2008/0255642 | A1* | 10/2008 | Zarins | A61N 5/0622 607/99 |
| 2011/0118736 | A1* | 5/2011 | Harper | A61B 5/1076 606/51 |
| 2011/0238062 | A1* | 9/2011 | Koss | A61B 18/18 606/34 |
| 2012/0283731 | A1* | 11/2012 | Unger | A61B 18/1206 606/49 |
| 2014/0025061 | A1 | 1/2014 | Benamou | |
| 2015/0032100 | A1* | 1/2015 | Coulson | A61B 5/0538 606/35 |
| 2015/0282867 | A1* | 10/2015 | Keller | A61B 18/1445 606/52 |
| 2016/0287316 | A1* | 10/2016 | Worrell | A61B 18/1482 |
| 2016/0310204 | A1* | 10/2016 | McHenry | A61B 18/1233 |
| 2016/0346034 | A1* | 12/2016 | Arya | A61B 18/22 |
| 2018/0036065 | A1* | 2/2018 | Yates | A61B 18/1482 |

\* cited by examiner

BIPOLAR ELECTROSURGICAL INSTRUMENTS

The present invention relates to bipolar electrosurgical instruments.

BACKGROUND OF THE INVENTION

Bipolar surgical instruments are used to clamp and seal tissue, such as blood vessels, during surgical procedures. Clamping is typically achieved using a pair of opposed jaws that are remotely operable to clamp around the vessel being sealed. Sealing is typically achieved using application of radio frequency energy delivered to the tissue being sealed by electrodes mounted on the opposed jaws of the instrument.

Existing designs of such instruments may not provide optimal transfer of electrical power to the tissue, and so may not provide optimal tissue sealing. For example, it is desirable to have acceptably short sealing times.

It is, therefore, desirable to provide an improved bipolar surgical instrument that, at least partially, addresses these drawbacks.

SUMMARY OF THE INVENTION

Aspects of the present invention are set out in the attached claims.

According to one exemplary aspect, there is provided an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, wherein the controller is operable to control the radio frequency generator to supply a radio frequency signal of a predetermined power level to the first and second electrodes for a predetermined time period having an end time, and to measure a voltage level between the first and second electrodes at the end time, the voltage level being stored as a starting voltage for subsequent supply of radio frequency signals to the first and second electrodes.

In one example, the controller is operable, subsequent to the sealing stage, and when such a comparison signal is indicative of the measured impedance level being less than to the predetermined reference impedance level to repeat the heating and sealing stages until the comparison signal is indicative of the measured impedance level being greater than or equal to the predetermined reference impedance level.

In one example, the controller is operable, in a completion stage subsequent to the sealing stage, and when the comparison signal is indicative of the measured impedance level being greater than or equal to the predetermined reference impedance level to control the radio frequency signal generator to apply a radio frequency signal at a predetermined completion voltage level, lower than the predetermined sealing voltage level, for a predetermined completion time period; and to end supply of such radio frequency signals.

According to another exemplary aspect, there is provided a method of operating an electrosurgical system comprising a bipolar electrosurgical instrument comprising a body; an elongate shaft attached to the body, the elongate shaft extending to a distal end; first and second elongate jaw members located at the distal end of the elongate shaft, and carrying respective first and second electrodes, the jaw members being movable relative to one another between an open position in which the first and second electrodes are spaced apart from one another, and a closed position in which the first electrode is adjacent the second electrode; and a power cable having a pair of electrically conductive elements, and having a first end for connection with a source of radio frequency electromagnetic energy, and a second end for connection to the first and second electrodes; and a waveform generator connected with the power cable of the bipolar electrosurgical instrument and comprising a radio frequency signal generator operable to supply a radio frequency signal to the first and second electrodes via the power cable; and a controller operable to control operation of the radio frequency signal generator, in dependence upon a received control input, supplying a radio frequency signal of a predetermined power level to the first and second electrodes for a predetermined time period having an end time; measuring an impedance level between the first and second electrodes at the end time; comparing the measured impedance with a predetermined reference impedance to produce a comparison signal; and determining a next mode of operation for the radio frequency generator in dependence upon such a comparison signal.

In one example, the method further comprises, subsequent to the sealing stage, and when such a comparison signal is indicative of the measured impedance level being less than to the predetermined reference impedance level repeating the heating and sealing stages until the comparison signal is indicative of the measured impedance level being greater than or equal to the predetermined reference impedance level.

In one example, the method further comprises, subsequent to the sealing stage, and when the comparison signal is indicative of the measured impedance level being greater than or equal to the predetermined reference impedance level a completion stage comprising controlling the radio frequency signal generator to apply a radio frequency signal at a predetermined completion voltage level, lower than the predetermined sealing voltage level, for a predetermined completion time period; and ending supply of such radio frequency signals.

DETAILED DESCRIPTION OF THE PREFERRED EMBODIMENTS

Figure 1:
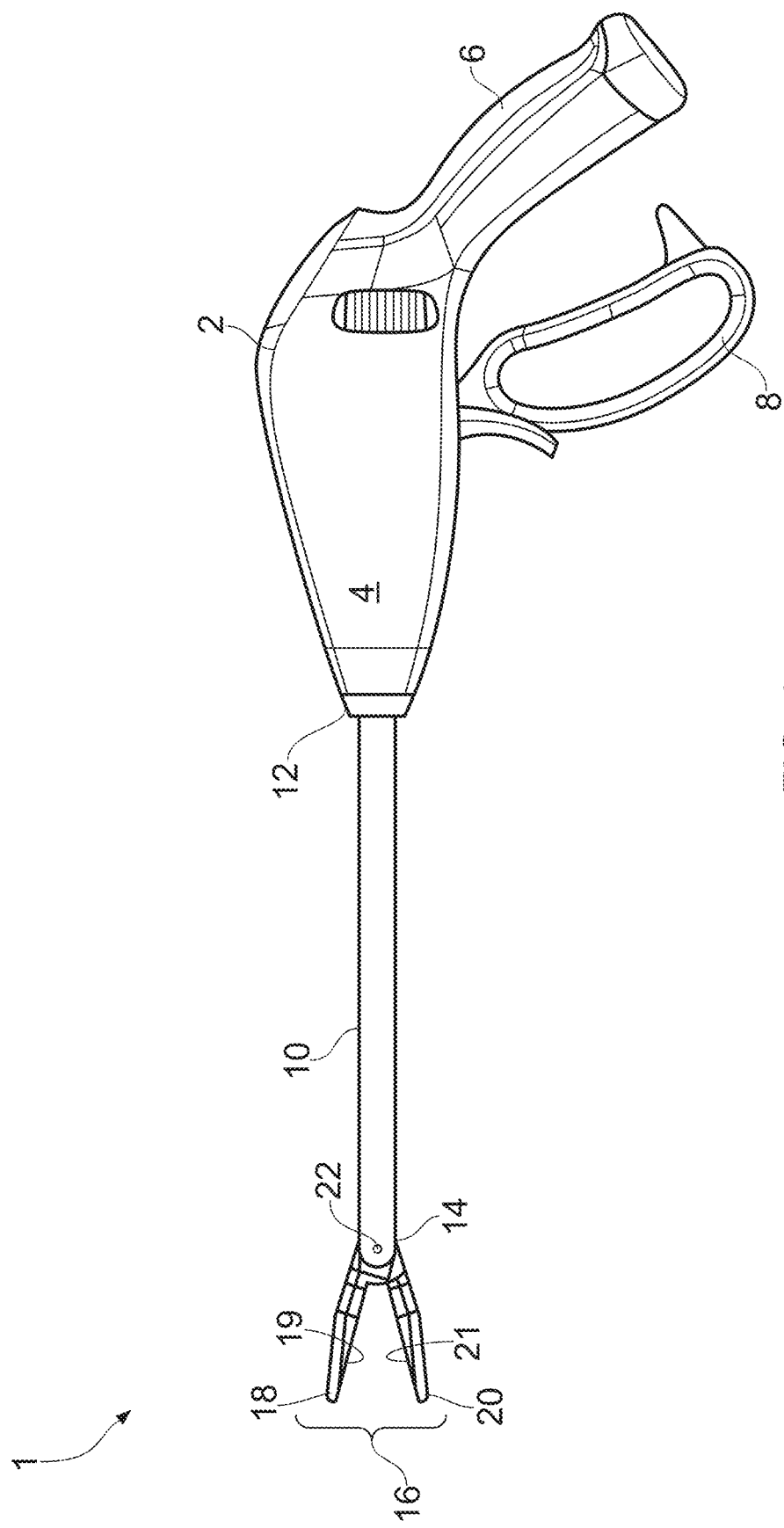
FIGS. 1 and 2 show side views of a bipolar surgical instrument embodying one aspect of the present invention in open and closed positions respectively.
Figure 2:
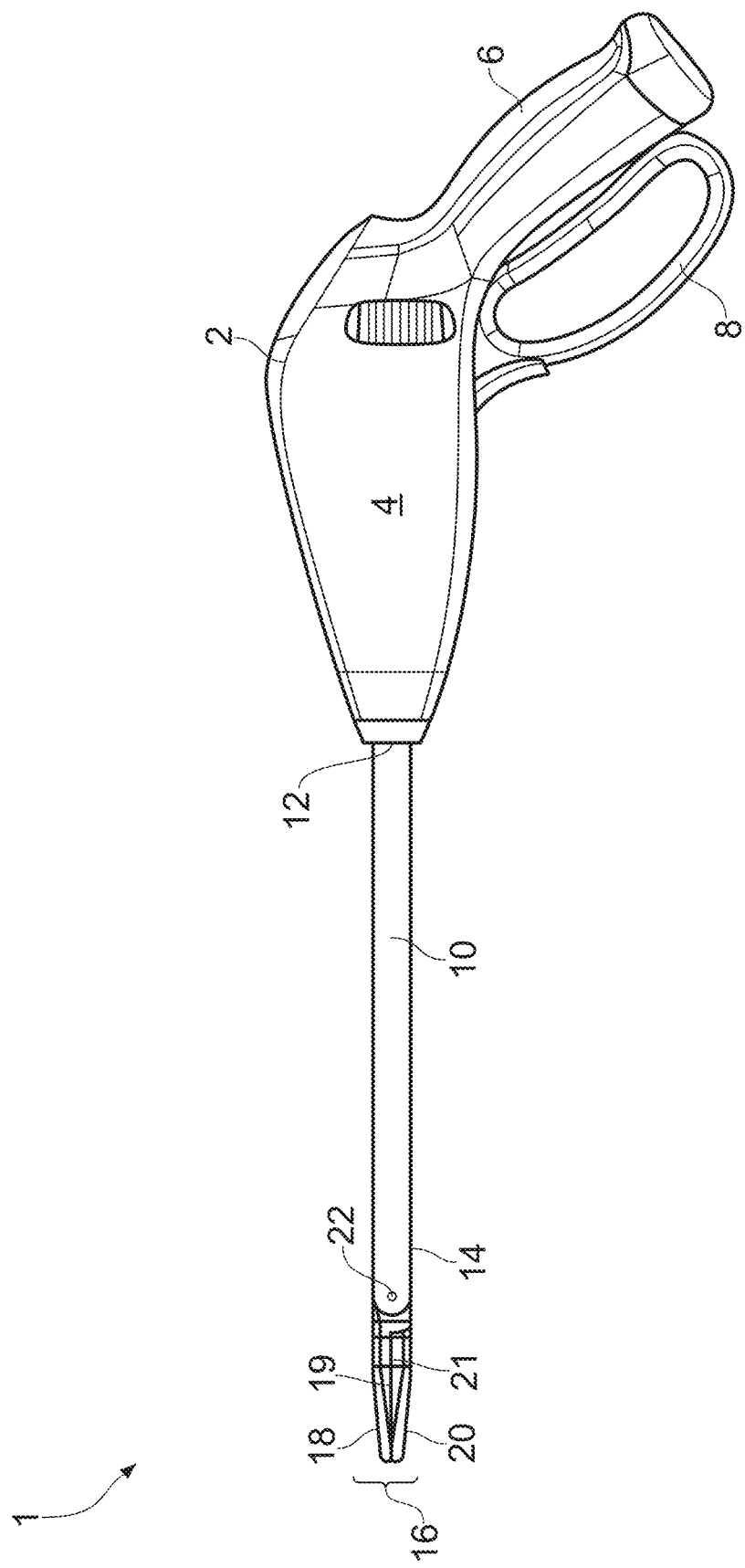

An example bipolar surgical instrument 1 is shown schematically in FIGS. 1 and 2. FIG. 1 illustrates an open position of the instrument 1, and FIG. 2 illustrates a closed position thereof.

The instrument 1 comprises a body 2 having a main housing 4 from which a fixed grip 6 extends. The fixed grip 6 is held during use by the operator of the instrument 1. A movable actuation grip 8 is movably mounted on the main housing 4 of the body 2. An elongate shaft 10 is attached to the main housing 4 of the body 2 and extends from a proximal end 12 at the main housing 4, to a distal end 14 of the shaft 10. The shaft 10 defines a longitudinal axis therealong, and an elongate passage extends from the proximal end 12 to the distal end 14 of the shaft 10.

A pair 16 of opposed jaws are located at the distal end 14 of the shaft 10. The pair 16 of jaws comprises a first jaw 18 and a second jaw 20. In the example of FIGS. 1 and 2, the first and second jaws 18 and 20 are pivotally mounted on a jaw pivot 22. The first and second jaws 18 and 20 are pivotable about the jaw pivot 22, between an open position (as shown in FIG. 1) in which the jaws 18 and 20 are separated from one another, and a closed position (as shown in FIG. 2) in which the jaws 18 and 20 are adjacent one another. In another example of a bipolar instrument embodying the present invention, only one of the jaws is movable. In another example, the movable jaw or jaws may be movable in any suitable manner, for example linearly, or in a combination of rotation and linear movement. The exact nature of the movement of the jaws is not important in the context of the present invention.

The first and second jaws 18 and 20 carry first and second electrodes 19 and 21 respectively. The first and second electrodes 19 and 21 are arranged to apply radio frequency electromagnetic energy to vessel held between the first and second jaws 18 and 20.

In use, the operator of the instrument 1 moves the actuation grip 8 from a first position (shown in FIG. 1) to a second position (shown in FIG. 2) in order to move the jaws 18 and 20 from the open position to the closed position. During an operation, vessel to be sealed is held between the jaws 18 and 20 in the closed position for a predetermined time period, with pressure applied by the operator, and with radio frequency energy applied to the vessel. The radio frequency energy serves to seal the held vessel.

Figure 3:
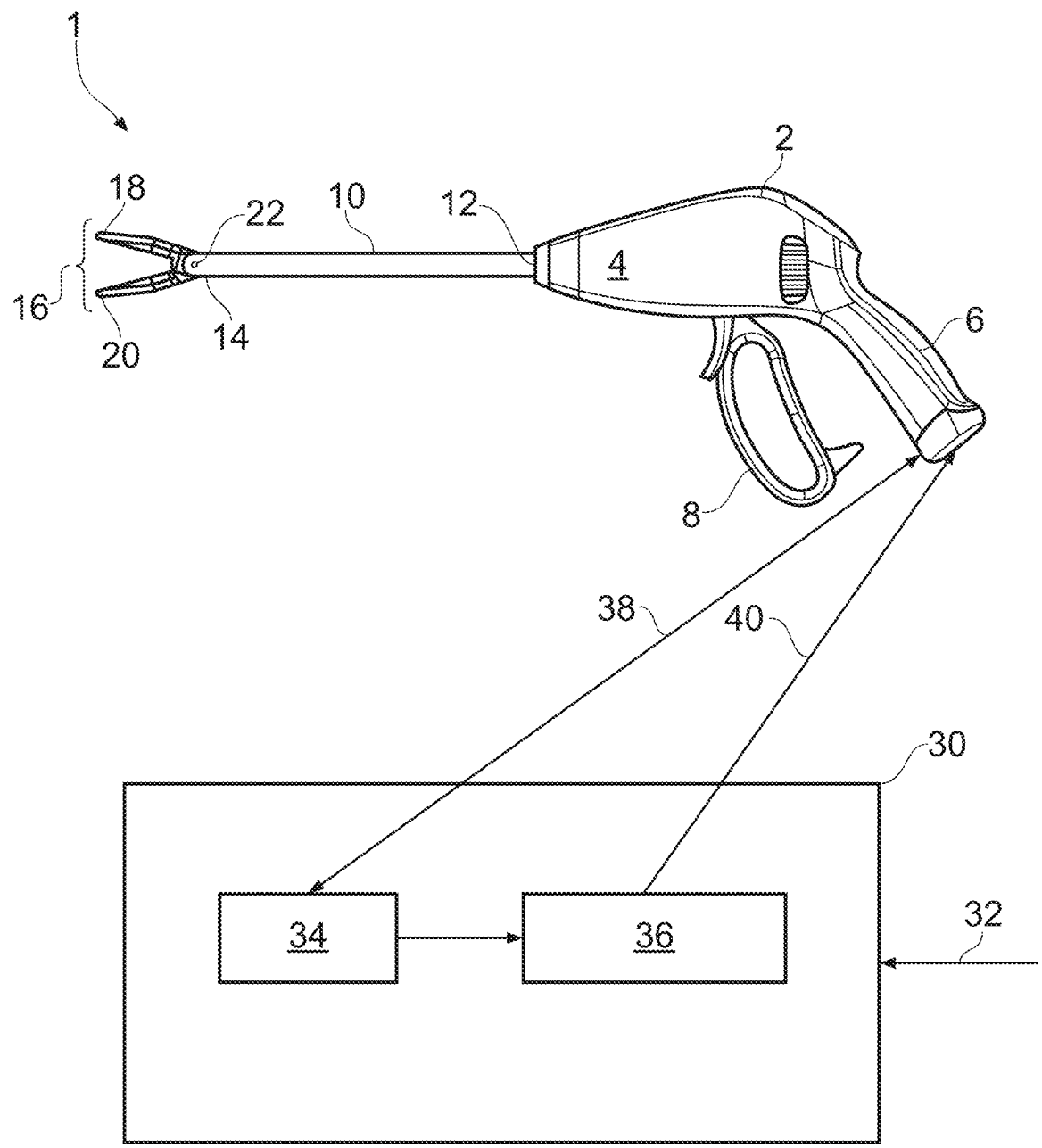
FIG. 3 illustrates a controller for use with a bipolar surgical instrument.

FIG. 3 illustrates the instrument 1 connected with a waveform generator 30. The waveform generator 30 receives an electrical power supply 32 and includes a controller 34 and a radio frequency signal generator 36. A control cable 38 connects the controller 34 to control inputs located, in one example, in or on the instrument 1. The control inputs may be located separately from the instrument 1, for example as a foot switch. A measurement cable may also be provided to provide a path for measurement signals.

The controller 34 is operable to control the signal generator 36 which is connected by power cable 40 to the instrument 1. The power cable 40 includes a pair of conductors that are connected to respective ones of the first and second electrodes 19 and 21 of the instrument 1. Upon reception of an appropriate control signal, for example from an operating switch such as a foot pedal, the controller 34 causes the signal generator 36 to supply a radio frequency electrical output signal via the power cable 40 to the first and second electrodes 19 and 21. One of the electrodes is defined as the active electrode and one as the return electrode.

The output radio frequency electrical signal in a system embodying the principles of present invention applies a desired sealing waveform to the vessel being held between the first and second jaws 18 and 20, which will be described below.

Figure 4:
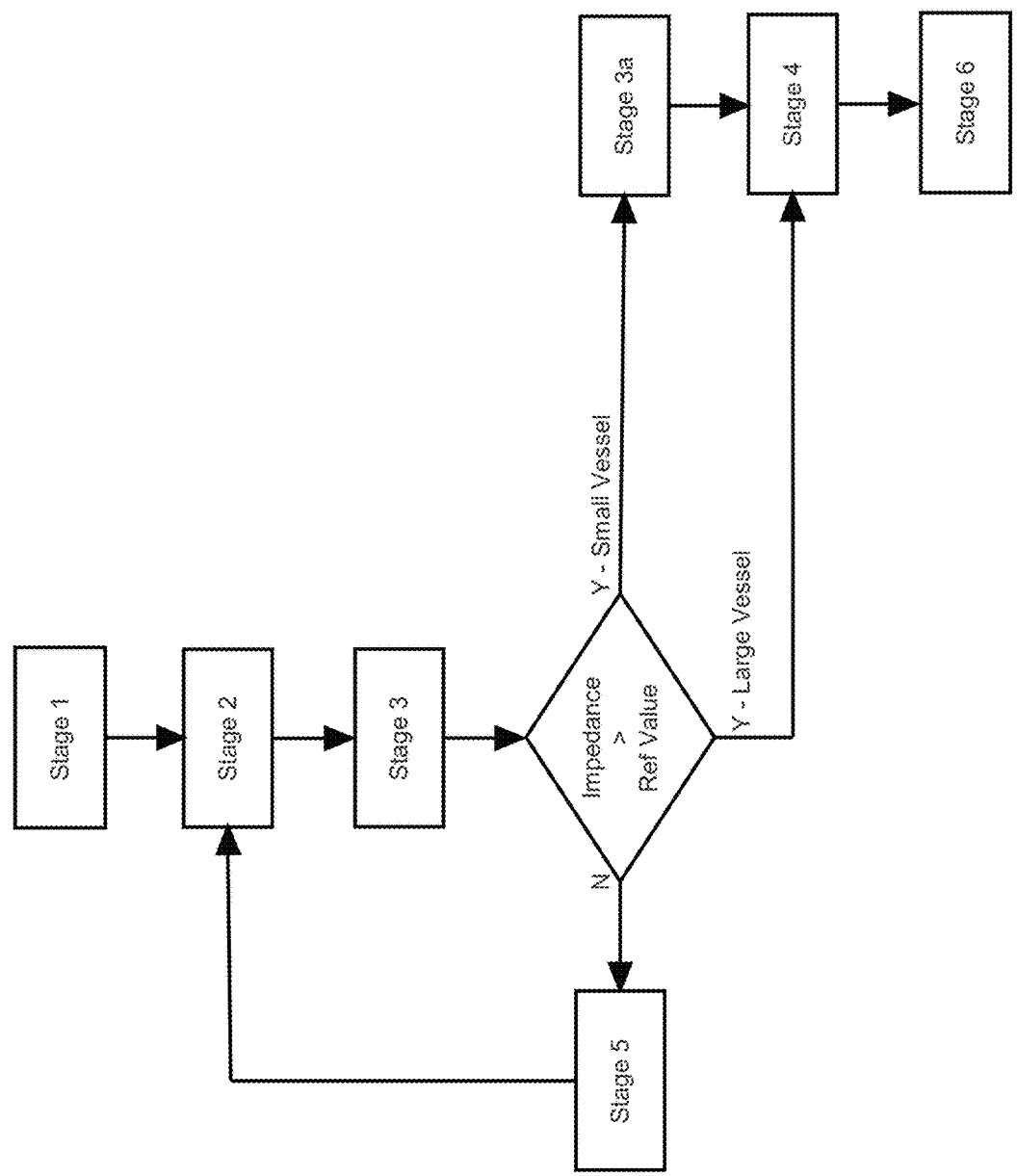
FIG. 4 is a flowchart illustrating steps in a method embodying another aspect of the present invention.
Figure 5:
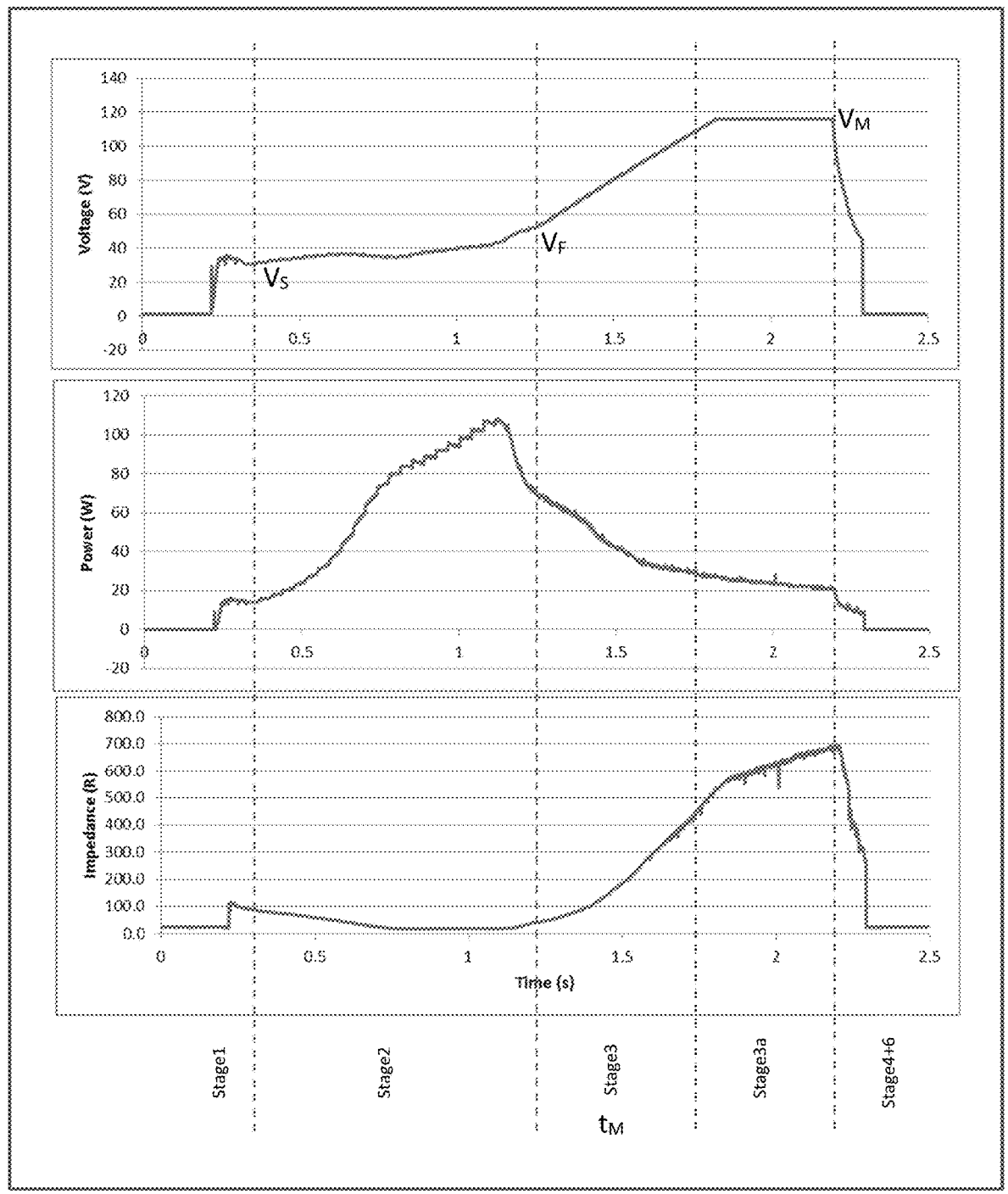
FIGS. 5 and 6 show graphs illustrating voltage, power and impedance against time for a bipolar surgical instrument operated in accordance with the method of FIG. 4.
Figure 6:
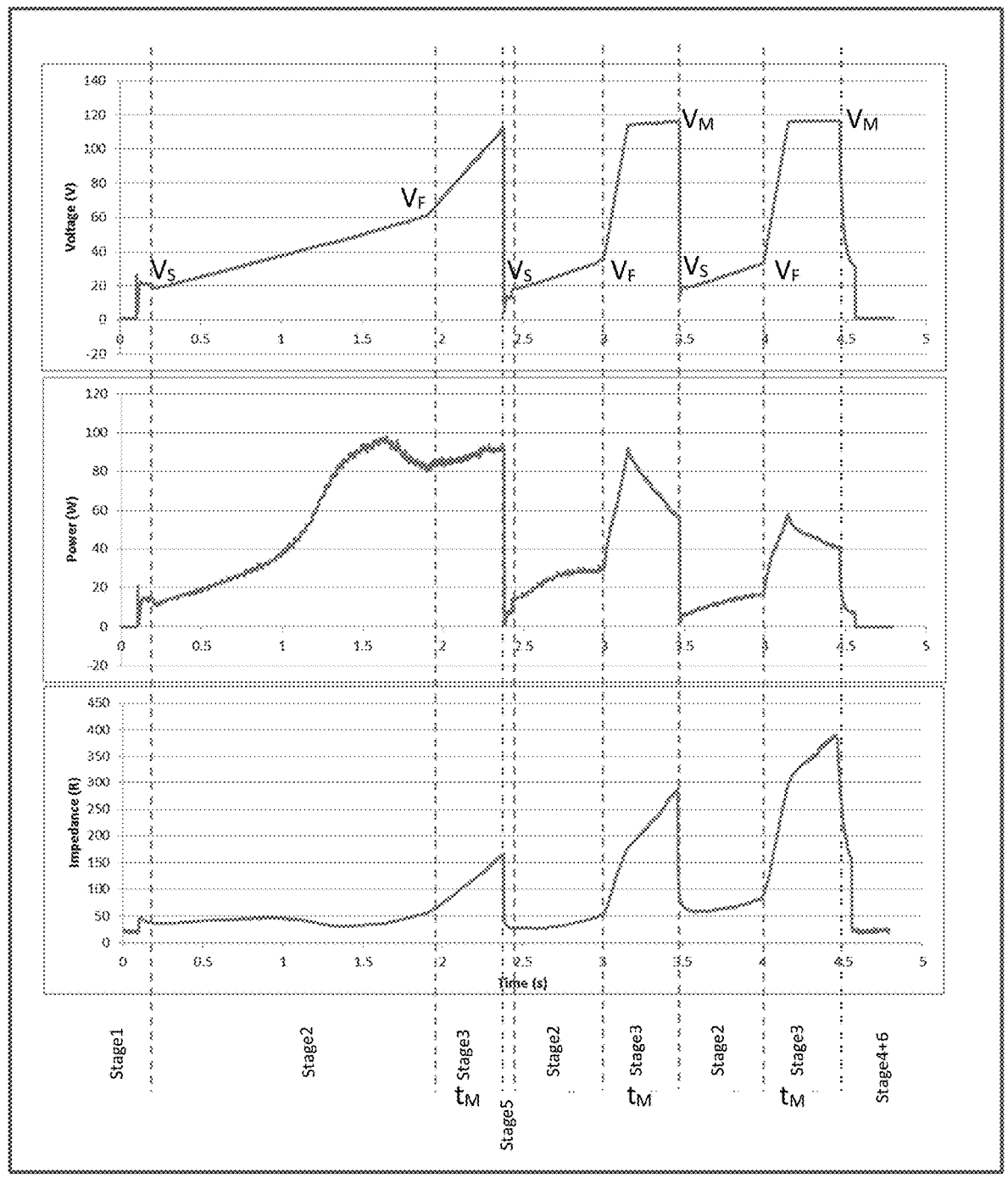

A method embodying one aspect of the present invention will now be described with reference to the flowchart of FIG. 4, and the graphs of FIGS. 5 and 6. The graphs of FIGS. 5 and 6 show exemplary voltage and power of the applied radio frequency signal, and exemplary measured impedance across the first and second electrodes of the surgical instrument 1.

In an embodiment of the present invention, stage 1 of the application of the radio frequency energy is an initial low-power stage, in which an appropriate starting voltage is determined. In stage 1, a constant power is applied to the vessel for a period of time short enough not to alter substantially the characteristics of the vessel. The constant power level may be in the range of up to 20 W, and may be applied for up to 200 ms. After the time period of application of the constant power level, the voltage required to maintain the initial power level is measured and is then used as the starting voltage $V_S$ for the vessel heating and sealing process.

Stage 2 applies a slow-ramping voltage across the first and second electrodes, which ramps up from the starting voltage determined in stage 1. Preferably, the applied voltage ramps in a linear manner. In one example, the voltage is ramped up from the starting voltage $V_S$ in discrete steps every millisecond. In one example, the voltage ramp rate is 0.02V/ms.

In order to determine when the boiling point of the vessel has been reached, without the need for a direct temperature measurement, the impedance of the vessel held between the jaws is measured. As pressure is applied to the vessel between the jaws, and the applied voltage increases, initially the impedance of the vessel drops. After an undefined time period, the vessel starts to coagulate, and the impedance increases from a minimum value.

In stage 2 of the present process, impedance is measured effectively continually, for example every 1 ms, as the applied voltage is ramped up. Each new impedance measurement is compared with a stored minimum impedance measurement for stage 2, and, if the new impedance measurement is lower than that previous impedance measurement, the new impedance measurement is stored as the minimum impedance measurement for stage 2. The impedance measurements continue during stage 2 until stage 2 is complete. The stored minimum impedance measurement at the end of stage 2 is then considered to be the minimum impedance level for stage 2 of the process.

Stage 2 is considered to be completed when the new impedance measurement is greater than the stored minimum impedance measurement by a predetermined value. For example, the predetermined value may be an absolute value of impedance, for example 20 R, or may be a proportion of the minimum impedance vale, such as 10%. When the initial stage 2 of the process is completed, then stage 3 commences.

Stage 3 of the process is a sealing and size detection process and takes place over a fixed hold time period $t_M$, for example 500 ms. During stage 3, the applied voltage is ramped-up from the final voltage $V_F$ applied at the end of stage 2, at a rate faster than that used during stage 2, towards a maximum voltage $V_M$, for example 115V. The applied voltage at the end of the stage 3 may not have reached the maximum voltage $V_M$, for example if $V_F$ is lower than expected, and the rate of increase of the applied voltage is not high enough to reach $V_M$. At the end of the hold time period, the impedance of the vessel is measured.

If the impedance is greater than a predetermined value, for example 200 R, 400 R, or greater, then the vessel size is determined to be small, and the applied voltage is ramped up to the maximum level $V_M$ or held at the maximum level $V_M$ for an additional hold-time, for example 500 ms, in stage 3a.

For such small vessel sizes the process moves to stage 4, which is a seal-completed check. Initial stage 4 impedance is measured, and applied power is reduced to a predetermined low power level $P_L$, for example 5 W, for a predetermined check time $t_C$, for example 100 ms. The impedance is then measured. If the measured impedance value is lower than the initial stage 4 impedance, then the seal is determined as being made correctly, and the process moves to stage 6. If the measured impedance is greater than the initial stage 4 impedance, then the seal is determined to be incomplete, and an error generated before the process moves to stage 6. The resulting waveform for smaller vessels is shown in FIG. 5.

For larger vessel sizes, as determined by an impedance less than a predetermined value, for example up to 400 R, at the end of stage 3, a re-ramping sequence is commenced by moving the process to stage 5. In stage 5, applied power is reduced, for example to 5 W, for a fixed period, for example 50 ms. Upon completion of this time period, the process repeats stages 2 and 3, in which the applied voltage is ramped up from the start voltage $V_S$. Stages 2 and 3 are repeated until the measured impedance is greater than or equal to a predetermined end-point impedance at the end of stage 3, for example 350 R. The process moves to stage 4, as for smaller vessels if the end point impedance is reached. The resulting waveform for larger vessels is shown in FIG. 6.

At stage 6, the radio frequency energy is terminated.

During the application process, the system monitors for open circuit faults, using the impedance measurements. If the impedance measurements are above a predetermined threshold value for a predetermined time period, an open-circuit condition is detected. For example, if the impedance is consistently above 1500 R for periods of 400 ms, then an open circuit is detected.

Similarly, during the application process, the system monitors for short circuit faults, using current measurements. If the current flow is greater than a predetermined threshold value for a predetermined time period, then a short-circuit condition is detected. The current threshold value is set to be higher than the current supplied during normal operating times.

For example, if the current is consistently above 4.5 A RMS, for periods of 400 ms, then a short circuit is detected. Upon detection of a short circuit, the radio frequency power is shut off In such a manner, an embodiment of the present invention is able to provide improved vessel sealing characteristics for a bipolar electrosurgical instrument.

The invention claimed is:

1. An electrosurgical system comprising:
a bipolar electrosurgical instrument comprising:
a body;
an elongate shaft attached to the body, the elongate shaft extending to a distal end;
a first elongate jaw member and a second elongate jaw member provided at the distal end of the elongate shaft, the first elongate jaw member carrying a first electrode and the second elongate jaw member carrying a second electrode, the first elongate jaw member and the second elongate jaw member being movable relative to one another between an open position in which the first electrode and the second electrode are spaced apart from one another, and a closed position in which the first electrode is adjacent the second electrode; and
a power cable having (1) a pair of electrically conductive elements, (2) a first end and (3) a second end for connection to the first electrode and the second electrode; and
a waveform generator connected with the first end of the power cable of the bipolar electrosurgical instrument and comprising:
a radio frequency signal generator operable to supply a radio frequency signal to the first electrode and the second electrode via the power cable; and
a controller operable to control operation of the radio frequency signal generator, in dependence upon a received control input,
wherein the controller is operable, in a sealing stage following, in seratium, a tissue impedance measurement stage and a heating stage:
to control the radio frequency signal generator to supply a radio frequency signal at a predetermined sealing voltage level to the first electrode and the second electrode for a sealing time period of a predetermined length having a sealing end time, the predetermined sealing voltage level being a voltage increase during the sealing time period such that the controller is configured to increase the voltage at a faster rate in the heating stage than in the tissue impedance measurement stage;
to measure an impedance level between the first electrode and the second electrode at the sealing end time;
to compare the measured impedance with a predetermined reference impedance to produce a comparison signal; and
to determine whether to repeat the heating and sealing stages or proceed to a different stage in dependence upon the comparison signal.

2. The electrosurgical system as claimed in claim 1, wherein the controller is operable, subsequent to the sealing stage, and when the comparison signal is indicative of the measured impedance level being less than the predetermined reference impedance;
to repeat the heating and sealing stages until the comparison signal is indicative of the measured impedance level being greater than or equal to the predetermined reference impedance.

3. The electrosurgical system as claimed in claim 1, wherein the controller is operable, in a completion stage subsequent to the sealing stage, and when the comparison signal is indicative of the measured impedance level being greater than or equal to the predetermined reference impedance;
to control the radio frequency signal generator to apply a radio frequency signal at a predetermined completion voltage level, lower than the predetermined sealing voltage level, for a predetermined completion time period; and to end supply of the radio frequency signal at the predetermined completion voltage level at the end of the predetermined completion time period.

4. A method of operating an electrosurgical system comprising a bipolar electrosurgical instrument comprising a body; an elongate shaft attached to the body, the elongate shaft extending to a distal end; a first elongate jaw member and a second elongate jaw member located at the distal end of the elongate shaft, the first elongate jaw member carrying a first electrode and the second elongate jaw carrying a second electrode, the first elongate jaw member and the second elongate jaw member being movable relative to one another between an open position in which the first electrode and the second electrode are spaced apart from one another, and a closed position in which the first electrode is adjacent the second electrode; and a power cable having (1) a pair of electrically conductive elements, (2) a first end and (3) a second end for connection to the first electrode and the second electrode; and a waveform generator connected with the first end of the power cable of the bipolar electrosurgical instrument and comprising a radio frequency signal generator operable to supply a radio frequency signal to the first electrode and the second electrode via the power cable; and a controller operable to control operation of the radio frequency signal generator, in dependence upon a received control input, wherein the method comprises in a sealing stage following, in seriatum, a tissue impedance measurement stage and a heating stage:

supplying a radio frequency signal of a predetermined power level to the first electrode and the second electrode for a predetermined time period having an end time, the predetermined power level resulting in a voltage increase during the predetermined time period, and increasing the voltage at a faster rate in the heating stage than in the tissue impedance measurement stage;

measuring an impedance level between the first electrode and the second electrode at the end time;

comparing the measured impedance with a predetermined reference impedance to produce a comparison signal; and determining whether to repeat the heating and sealing stages or proceed to a different stage in dependence upon the comparison signal.

5. The method as claimed in claim 4, further comprising, subsequent to the sealing stage, and when the comparison signal is indicative of the measured impedance level being less than the predetermined reference impedance; repeating the heating and sealing stages until the comparison signal is indicative of the measured impedance level being greater than or equal to the predetermined reference impedance.

6. The method as claimed in claim 4, further comprising, subsequent to the sealing stage, and when the comparison signal is indicative of the measured impedance level being greater than or equal to the predetermined reference impedance:

a completion stage comprising:
controlling the radio frequency signal generator to apply a radio frequency signal at a predetermined completion voltage level, lower than the predetermined sealing voltage level, for a predetermined completion time period; and
ending supply of the radio frequency signal at the predetermined completion voltage level at the end of the predetermined completion time period.

7. An electrosurgical system comprising:
a bipolar electrosurgical instrument comprising:
a body;
an elongate shaft attached to the body, the elongate shaft extending to a distal end;
first elongate jaw member and a second elongate jaw member at the distal end of the elongate shaft, the first elongate jaw member carrying a first electrode and the second elongate jaw member carrying a second electrode, the first elongate jaw member and the second elongate jaw member being movable relative to one another between an open position in which the first and second electrodes are spaced apart from one another, and a closed position in which the first electrode is adjacent the second electrode; and
a power cable having (1) a pair of electrically conductive elements, (2) a first end and (3) a second end for connection to the first electrode and the second electrode; and
a waveform generator connected with the first end of the power cable of the bipolar electrosurgical instrument and comprising:
a radio frequency signal generator operable to supply a radio frequency signal to the first electrode and the second electrode via the power cable; and
a controller operable to control operation of the radio frequency signal generator, in dependence upon a received control input,
wherein:
the controller is operable, in a sealing stage following, in seratium, a tissue impedance measurement stage and a heating stage:
to control the radio frequency signal generator to supply a radio frequency signal at a predetermined sealing voltage level to the first electrode and the second electrode for a sealing time period of a predetermined length having a sealing end time;
to measure an impedance level between the first electrode and the second electrode at the sealing end time;
to compare the measured impedance with a predetermined reference impedance to produce a comparison signal;
to determine a relative size of a vessel based on the comparison signal;
to determine whether to repeat the heating and sealing stages or proceed to a different stage in dependence upon the relative size of the vessel; and
when the comparison signal indicates that the measured impedance is greater than the predetermined reference impedance, the controller:
determines that the relative size of the vessel is small, and
commences supplying a radio frequency signal at a voltage level that increases to a maximum value.

8. The electrosurgical system as claimed in claim 7, wherein
when the comparison signal indicates that the measured impedance is less than the predetermined reference impedance, the controller:
determines that the relative size of the vessel is large, and
commences a stage of reducing the voltage for a fixed period and subsequently repeats the heating and sealing stages.

* * * * *